Dec. 11, 1951 S. POULSEN Plant Pat. 1,050
ROSE PLANT
Filed June 2, 1950
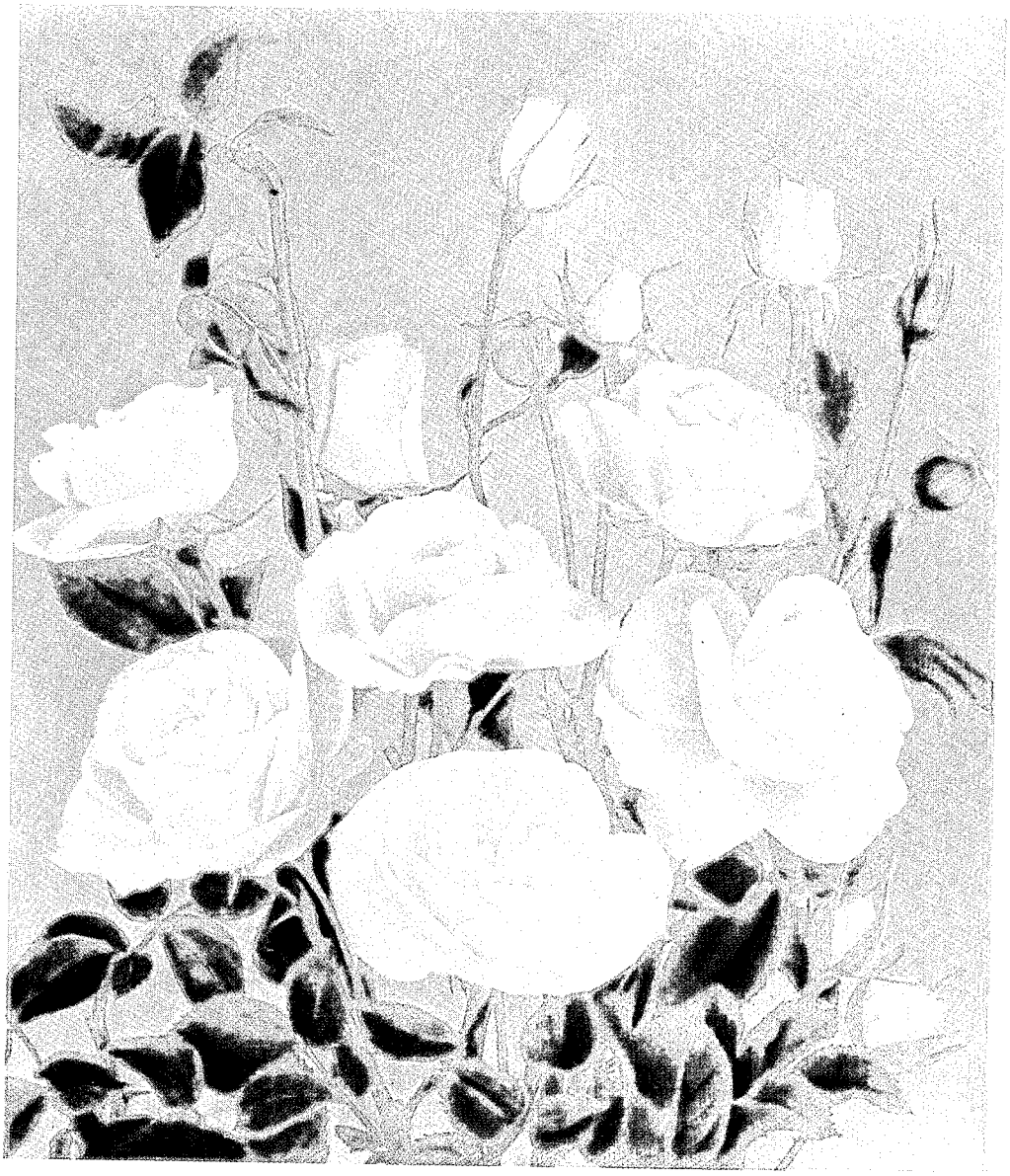
Inventor.
Svend Poulsen
By: Robb & Robb
Attorneys.

Patented Dec. 11, 1951

Plant Pat. 1,050

UNITED STATES PATENT OFFICE 1,050

ROSE PLANT

Svend Poulsen, Copenhagen, Denmark, assignor to The Conard-Pyle Company, West Grove, Pa., a corporation of Pennsylvania Application June 2, 1950, Serial No. 165,669

1 Claim. (Cl. 47—61)

The present invention relates to a new and distinct variety of rose plant of the hybrid polyantha class, originated by crossing the variety "Poulsen's Pink" (unpatented) × "Ophelia" (unpatented), and marking an important improvement in roses of this class.

The flowers of this new variety are double, with color tones like the more single blooming rose variety "Springtime" (Plant Patent No. 268).

This new variety is still further distinguished from its parents, as well as from other known varieties, by combining with the aforementioned color feature and flower habit, exceptionally strong, hardy, healthy and free-blooming habits of growth of the plants, and by its abundance of foliage, giving the plants bushiness.

Asexual reproduction of this new variety by budding at Copenhagen, Denmark, and at West Grove, Pennsylvania, U. S. A., shows that the foregoing characteristics come true to form and are established and transmitted through succeeding propagations.

The accompanying drawing shows specimens of the new variety, with the flowers in various stages of development from bud to full-open bloom.

The following is a detailed description of the new variety, with color terminology in accordance with Ridgway's Color Standards and Nomenclature, except where general color terms of ordinary dictionary significance are used:

Type: Hardy; bush; outdoor; seedling; for cut flowers and garden decoration.
Class: Hybrid polyantha.
Breeding: Seedling.
*Seed parent.* — "Poulsen's Pink" (unpatented).
*Pollen parent.*—"Ophelia" (unpatented).
Propagation: Holds its distinguishing characteristics through succeeding propagations by budding.

*Flower*

Locality where grown: West Grove, Pennsylvania.
Flowers borne: Several to stem; in irregular cluster; on strong, medium length stems.
Quantity of bloom: Abundant outdoors.
Continuity: Continuous.
Fragrance: Slight; tea.
Bud:
*Preduncle.*—Medium length; medium heavy; erect; yellowish green, often tinged with red; rough; medium number of red prickles.
*Before calyx breaks.* — Size — medium. Form—pointed; ovoid; with foliaceous appendages on the surface of the bud; with little cut foliaceous parts extending beyond the tip of the bud equal to one-fourth or more of its length.

*As calyx breaks.*—Color—Carmine, Plate I.
*As first petal opens.* — Size — medium. Form — medium length; cup-shaped. Color — outside: Eosine Pink, Plate I, tinged with Carmine, Plate I; inside: Shrimp Pink, Plate I; Empire Yellow, Plate IV, at base; sometimes with tinges of Spinel Red, Plate XXVI, at apex.
*Opening.*—Opens up well.
Bloom:
*Size when fully open.*—Medium large; 2½ inches to 3½ inches.
*Petalage.*—Double; from 24 to 32 petals; arranged regularly.
*Form.*—Cupped at first; petals being at first tightly cupped inward; becoming later, at maturity, loosely cupped.
Petals: Medium thick; with inside satiny and outside shiny.
*Shape.*—Outer—obovate, with apex almost flat. Intermediate—obovate, with apex almost flat. Inner—obovate, with apex almost flat.
*Color.*—Colors may be modified by being shaded or washed with other colors; also colors become lighter with age.

This description of a newly opened flower was made from a rose grown outdoors in the month of November, 1949, at West Grove, Pennsylvania:

*Color.*—Outside petal—outside surface: Hermosa Pink, Plate I; sometimes with shadings of Eosine Pink, Plate I; sometimes with tinges of Spinel Red, Plate XXVI; inside surface: Shrimp Pink, Plate I; Empire Yellow, Plate IV, at base; sometimes with tinges of Spinel Red, Plate XXVI, at apex. Intermediate petal—outside surface: Eosine Pink, Plate I; sometimes with shadings of Begonia Rose, Plate I; Pinard Yellow, Plate IV, at base; inside surface: Shell Pink, Plate XXVIII; Pinard Yellow, Plate IV, at base. Inner petal—outside surface: Geranium Pink, Plate I, to Begonia Rose, Plate I; Pinard Yellow, Plate IV, at base; inside surface: Pale Congo Pink, Plate XXVIII; Pinard Yellow, Plate IV, at base.

This description was made from a rose that was open for three days outdoors in the month of November, 1949, at West Grove, Pennsylvania:

*Color.*—Outer petal—outside surface: Deep Rose Pink, Plate XII; frequently with tinges of Amaranth Purple, Plate XII; Pale Seafoam Green, Plate XXXI, at base; inside surface: Cameo Pink, Plate XXVI, with shadings of white at base; sometimes with tinges of Deep Rose Pink, Plate XII. Inner petal—outside surface: Deep Rose Pink, Plate XII; inside surface: Cameo Pink, Plate XXVI; shading to white at the base.

*General color effect.*—Newly opened flower—Light Hermosa Pink, Plate I, at edges with shadings of Bosine Pink, Plate I, and light Begonia Rose, Plate I, toward center. Three days open—Cameo Pink, Plate XXVI.

*Behavior.*—Persist; fading white then brown.

*Flower longevity.*—Cut roses grown in greenhouse kept at living room temperatures—4 to 5 days in November.

*Reproductive organs*

Stamens: Medium to many; most arranged regularly about pistils.

Filaments: Most with anthers; some short; some medium length; yellow.

Anthers: All open at once; medium size; yellow gold; occasionally an anther fused with a petaloid.

Pollen: Moderate; yellow gold.

Pistils: Medium number.

Styles: Almost even; medium length; medium heavy; bunched and columnar.

Stigma: Greenish white.

Ovaries: All enclosed in calyx.

Hips: Medium length; globular; walls medium thick; green, outside color frequently tinged with red.

Sepals: Permanent; medium length; spear-shaped.

Seeds: Medium number; medium size.

*Plant*

Foliage:

*Leaves.*—Compound of five to seven leaflets; abundant; medium size; leathery.

*Leaflets.*—Shape—oval, with apex acute; base round; margin simply serrate.

*Color.*—*Mature* — Upper surface — Cedar Green, Plate VI; under surface—Rainette Green, Plate XXXI. *Young*—upper surface—Dark Cedar Green, Plate VI; Garnet Brown, Plate I, at very edges; under surface—Light Cress Green, Plate XXXI; Garnet Brown, Plate I, at very edges.

*Rachis.*—Medium heavy. Upper side—grooved. Under side—sparsely thorny.

*Stipules.*—Medium length; medium width; with medium length points turning out at an angle of less than 45°.

*Disease.*—Resistant to mildew and blackspot.

Growth:

*Habit.*—Bushy; upright; branched.

*Growth.*—Vigorous.

*Canes.*—Heavy.

*Main stems.*—Green to gray green. Thorns—several; medium length; hooked downward; with medium length oval base; incipient thorns among normal-sized thorns. Prickles—brown; several. Hairs—none.

*Branches.*—Green to gray green. Thorns—several; medium length; hooked downward; with medium length oval base; incipient thorns among normal-sized thorns. Prickles—several; brown. Hairs—none.

*New shoots.*—Yellowish green often tinged with red. Thorns—several; medium length; hooked downward; with short to medium length oval base. Prickles—few; reddish. Hairs—none.

I claim:

A new and distinct variety of rose plant of the hybrid polyantha class, characterized as to novelty by the double form of the flowers with color tones comparable to the variety "Springtime" (Plant Patent No. 268), by the exceptionally strong, hardy, healthy and free blooming habits of growth of the plants, and by its abundance of foliage, giving the plants bushiness, substantially as shown and described.

SVEND POULSEN.

No references cited.